United States Patent [19]

Kelly

[11] 4,206,304
[45] Jun. 3, 1980

[54] ESTERS OF 9-DEOXY-6,9 α-EPOXYMETHANO-PG ANALOGS

[75] Inventor: Robert C. Kelly, Kalamazoo, Mich.

[73] Assignee: The Upjohn Company, Kalamazoo, Mich.

[21] Appl. No.: 941,814

[22] Filed: Sep. 11, 1978

Related U.S. Application Data

[62] Division of Ser. No. 788,145, Apr. 19, 1977, Pat. No. 4,130,569.

[51] Int. Cl.$^2$ ............................................. C07D 311/02
[52] U.S. Cl. ................................ 542/426; 260/345.2; 542/429
[58] Field of Search .................... 260/345.2; 542/426, 542/429

[56] References Cited

U.S. PATENT DOCUMENTS 4,123,441  10/1978  Johnson .............................. 260/345.2

OTHER PUBLICATIONS

Pace-Asciak et al., Biochem., 10, 3657 (1971).
Pace-Asciak et al., JACS. 98, 2348 (1976).

*Primary Examiner*—Nicky Chan
*Attorney, Agent, or Firm*—Morris L. Nielsen; Robert A. Armitage

[57] ABSTRACT

Processes for preparing prostacyclin analogs which are 9-deoxy-6,9-epoxymethano derivatives of prostaglandin $F_{1\alpha}$-type compounds, illustrated, for example, by a compound of the formula

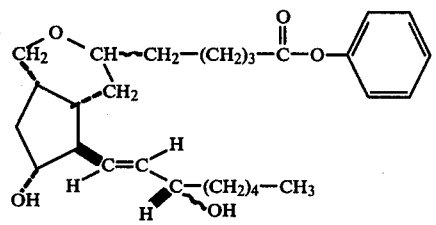

wherein ~ indicates alpha or beta configuration; including the products and intermediates produced therein, said products having pharmacological utility.

12 Claims, No Drawings

ESTERS OF 9-DEOXY-6,9 α-EPOXYMETHANO-PG ANALOGS

CROSS REFERENCE TO RELATED APPLICATIONS

The present application is a divisional application of Ser. No. 788,145, filed Apr. 19, 1977, now issued as U.S. Pat. No. 4,130,569, on Dec. 19, 1978.

The present invention relates to prostaglandin analogs for which the essential material constituting a disclosure therefor is incorporated by reference here from U.S. Pat. No. 4,130,569.

I claim:

1. A cyclic ether of the formula

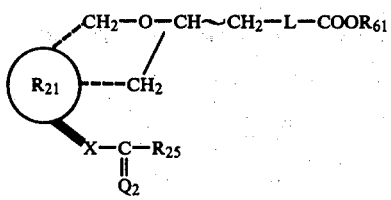

wherein L is (1) a valence bond, (2) $-(CH_2)_d-$ wherein d is one to 5 inclusive, (3) $-(CH_2)_t-CF_2-$ wherein t is 2, 3, or 4, (4) $-CH_2CH=CH-A-$ wherein A is a valence bond or $-(CH_2)_h-$ wherein h is one, 2, or 3, or (5) $-CH_2-O-CH_2-Y-$ wherein Y is a valence bond or $-(CH_2)_k-$ wherein k is one or 2; wherein $Q_2$ is

wherein $R_3$ is hydrogen or alkyl of one to 4 carbon atoms, inclusive, wherein $R_{21}$ is

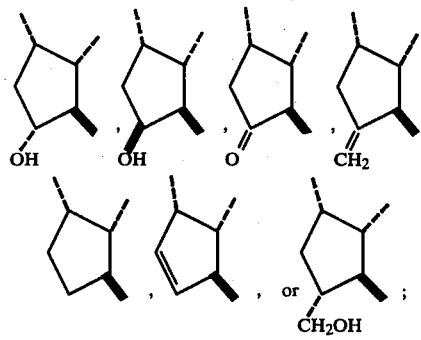

wherein $R_{25}$ is

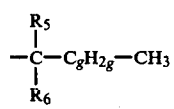

wherein $C_gH_{2g}$ is alkylene of one to 9 carbon atoms, inclusive, with one to 5 carbon atoms, inclusive, in the chain between $-CR_5R_6-$ and terminal methyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro;

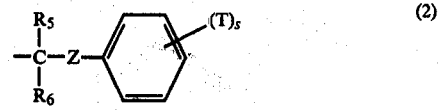

wherein $R_5$ and $R_6$ are as defined above with the proviso that neither $R_5$ nor $R_6$ is fluoro when Z is oxa (—O—); wherein Z represents an oxa atom (—O—) or $C_jH_{2j}$ wherein $C_jH_{2j}$ is a valence bond or alkylene of one to 9 carbon atoms, inclusive, substituted with zero, one, or 2 fluoro, with one to 6 carbon atoms, inclusive, between $-CR_5R_6-$ and the phenyl ring; wherein T is alkyl of one to carbon atoms, inclusive, fluoro, chloro, trifluoromethyl, or $-OR_7$ wherein $R_7$ is alkyl of one to 4 carbon atoms, inclusive, and s is zero, one, 2, or 3, with the proviso that not more than two T's are other than alkyl and when s is 2 or 3 the T's are either the same or different; or

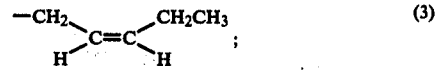

wherein $R_{61}$ is (a) cycloalkyl of 3 to 10 carbon atoms, inclusive, (b) aralkyl of 7 to 12 carbon atoms, inclusive, (c) phenyl, (d) phenyl substituted with one, 2, or 3 chloro or alkyl of one to 4 carbon atoms, inclusive;

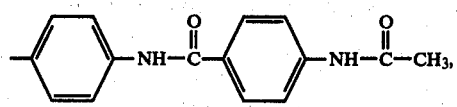

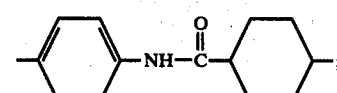

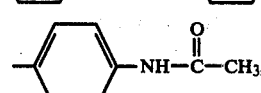

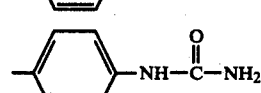

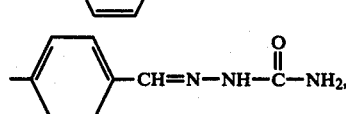

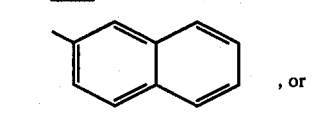

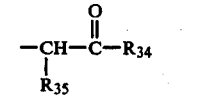

wherein $R_{34}$ is phenyl, p-bromophenyl, p-biphenylyl, p-nitrophenyl, p-benzamidophenyl, or 2-naphthyl, and wherein $R_{35}$ is hydrogen or benzoyl;

wherein X is cis- or trans-$-CH=CH-$, $-C\equiv C-$, or $-CH_2CH_2-$; and wherein the wavy line (∼) indicates attachment in cis or trans configuration.

2. A compound according to claim 1 wherein X is trans—CH=CH—.

3. A compound according to claim 2 wherein $Q_2$ is

wherein $R_3$ is hydrogen, methyl, or ethyl.

4. A compound according to claim 3 wherein $R_{21}$ is

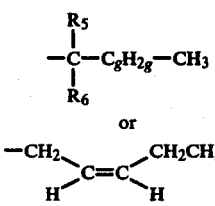

5. A compound according to claim 4 wherein L is —(CH$_2$)$_d$— wherein d is one to 5 inclusive.

6. A compound according to claim 5 wherein $R_{25}$ is $$-\underset{R_6}{\overset{R_5}{\underset{|}{\overset{|}{C}}}}-C_gH_{2g}-CH_3$$

or

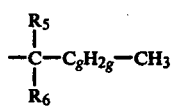

7. A compound according to claim 6 wherein $$-\underset{R_6}{\overset{R_5}{\underset{|}{\overset{|}{C}}}}-C_gH_{2g}-CH_3$$

is n-pentyl.

8. A compound according to claim 5 wherein $R_{25}$ is

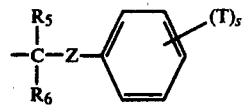

9. A compound according to claim 8 wherein

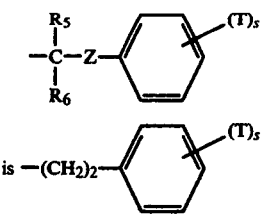

is —(CH$_2$)$_2$—⌬—(T)$_s$

10. A compound according to claim 8 wherein

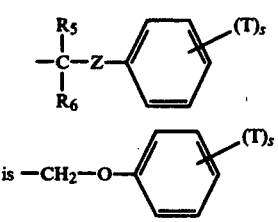

is —CH$_2$—O—⌬—(T)$_s$

11. A compound according to claim 4 wherein L is —(CH$_2$)$_t$—CF$_2$— wherein t is 2, 3, or 4.

12. A compound according to claim 3 wherein $R_{21}$ is

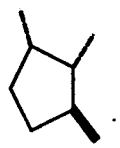

* * * * *

UNITED STATES PATENT OFFICE
CERTIFICATE OF CORRECTION

Patent No. 4,206,304　　　　　　　　　　Dated　　3 June 1980

Inventor(s)　Robert C. Kelly

It is certified that error appears in the above-identified patent and that said Letters Patent are hereby corrected as shown below:

Column 1, line 29, "-CH₂CH=CH-A-" should read -- -CH₂-CH=CH-A- --;

Column 2, lines 38-42,

Column 2, line 17, "alkyl of one to carbon atoms" should read -- alkyl of one to 4 carbon atoms --.

Signed and Sealed this

*Twenty-first* Day of *April 1981*

[SEAL]

*Attest:*

RENE D. TEGTMEYER

*Attesting Officer*　　*Acting Commissioner of Patents and Trademarks*